United States Patent [19]

Nethercutt

[11] 4,262,800
[45] Apr. 21, 1981

[54] STERILIZABLE HOLDER FOR FIBER OPTIC SURGICAL UNIT OR THE LIKE

[75] Inventor: Henry W. Nethercutt, Huntington, W. Va.

[73] Assignee: KEB Industries, Huntington, W. Va.

[21] Appl. No.: 65,215

[22] Filed: Aug. 9, 1979

[51] Int. Cl.³ .................. B65D 73/00; B65D 85/00; B65D 65/16
[52] U.S. Cl. .................. 206/364; 206/45.34; 206/478; 206/459; 206/805; 211/13
[58] Field of Search .......... 206/364, 363, 373, 45.34, 206/481, 478, 479, 483, 805, 459; 128/6; 211/13, 59.1; 248/89

[56] References Cited

U.S. PATENT DOCUMENTS

| 2,254,431 | 2/1941 | Levine | 206/364 |
| 2,645,340 | 7/1953 | Dow | 206/478 |
| 3,206,014 | 9/1965 | Blumberg | 206/45.34 |
| 3,464,545 | 9/1969 | Bailey | 206/478 |
| 3,633,758 | 1/1972 | Morse | 211/13 |
| 3,749,233 | 7/1973 | McCormick, Jr. | 206/373 |
| 3,878,939 | 4/1975 | Wilcox | 206/373 |
| 3,927,765 | 12/1975 | Beal | 206/481 |
| 4,146,019 | 3/1979 | Bass et al. | 128/6 |

*Primary Examiner*—William T. Dixson, Jr.
*Attorney, Agent, or Firm*—Le Blanc, Nolan, Shur & Nies

[57] ABSTRACT

A sterilizable holder for a fiber optic surgical unit or similar delicate medical instrument including a base, an outline of the instrument formed on the base, pairs of retainer pegs located about the outline on the base and elastic bands engaging the pegs to secure the instrument on the holder. The instrument outline may be etched on the base or printed onto the base. The base may be made of transparent plastic and all parts may be conventionally gas sterilized at temperatures of 135° F. or less.

2 Claims, 2 Drawing Figures

STERILIZABLE HOLDER FOR FIBER OPTIC SURGICAL UNIT OR THE LIKE

BACKGROUND OF THE INVENTION

This invention relates to support trays in the form of reusable holders and more particularly to a sterilizable holder for extremely delicate and expensive medical instruments such as fiber optic surgical units.

Such instruments are used in visual examination, diagnosis and treatment. These instruments have large lenses, connectors and a bundle of very delicate glass fibers and tubes within a small sheath. Even in normal, careful handling and sterilization they are easily broken with consequent repair costs as high as $2,000.00. The present invention provides a holder in the form of a tray of uncomplicated structure to which the instrument may be easily and readily secured and subsequently detached for use. Thus, possibilities of damage or breakage during normal handling and sterilization procedures are reduced to a minimum because the instrument always remains attached to the holder except when actually being used by the physician.

Several somewhat similar and sterilizable structures are taught by the following, prior U.S. Patents. A support plate having tubular guides for mounting a catheter is disclosed in U.S. Pat. No. 3,633,758 issued to P. H. Morse. However, a tubular guide configuration cannot be used with extremely delicate instruments such as fiber optic surgical units. Specifically, the relatively large lenses, connectors control section and associated accessories could not be supported by such a structure without damage to the unit. U.S. Pat. No. 3,983,996 issued to W. H. Hendren III discloses a sterilizable solid plastic body or case, recessed to receive a urological or similar telescope but the holder has considerable bulk in relation to the instrument and is unsuited for fiber optic surgical units having extended length cord and insertion tube sections which are coiled when not in use. Another sterilizable tray for holding instruments such as hardware, plates, etc. for orthopedic surgery is disclosed in U.S. Pat. No. 3,437,423 issued to D. G. Mondiadis. A similar tray for hypodermic needles and the like is disclosed in U.S. Pat. No. 2,472,028 issued to A. J. Son while a disposable medical instrument tray is shown in U.S. Pat. No. 3,013,656 issued to W. P. Murphy, Jr. More remote disclosures of apparatus for storing delicate items such as musical instrument reeds and ceramic objects are taught by U.S. Pat. Nos. 4,089,412 issued to K. Bough and 2,784,840 issued to J. Stefanik, respectively.

However, the prior art fails to disclose a sterilizable holder for fiber optic surgical units or the like, having a base with a precise outline of the instrument to be secured thereon formed on the base, and provided with a plurality of paired pegs or posts to retain the unit in place by means of elastic or rubber bands engaging the posts over the unit once it is located on the base.

SUMMARY OF THE INVENTION

Accordingly, it is a principal object of the invention to provide a reusable, sterilizable holder for very delicate medical instruments such as fiber optic surgical units, including a base structure having a precise outline of the instrument thereon whereby the possibility of erroneous mounting of the unit is negated.

It is an object of the invention to provide a sterilizable holder for fragile, medical instruments including a base with paired locating and retaining posts thereon for receiving the several parts of the instrument, which are then held securely in place on the base by elastic bands.

It is another object of the invention to provide a sterilizable holder for delicate medical instruments, made up of a transparent base having a precise outline of the instrument etched or printed onto the rear face of the base for assuring accurate, predetermined placement of the instrument on the holder.

It is a further object of the invention to provide a sterilizable holder for fragile, expensive medical instruments of uncomplicated, low cost construction, the components thereof being made of materials which will easily withstand a conventional gas sterilization procedure at temperatures up to 135° F.

Generally stated, the sterilizable holder disclosed and claimed herein includes a base having an outline of the instrument to be secured thereon. Paired sets of pegs or posts are arranged about the outline to facilitate placement of the instrument thereon, which is then secured in place by elastic bands stretched over the pegs of each paired set of pegs or posts. The base may be made of transparent material, the outline of the instrument being etched or printed onto the underside of the base. The holder with its instrument in place is wrapped and sterilized according to known procedures and then stored awaiting operating room use.

BRIEF DESCRIPTION OF THE DRAWINGS

Further and more complete objects and advantages of the instant invention will become apparent by reference to the following syecification and drawings in which.

DESCRIPTION OF THE PREFERRED EMBODIMENT

Figure 1:
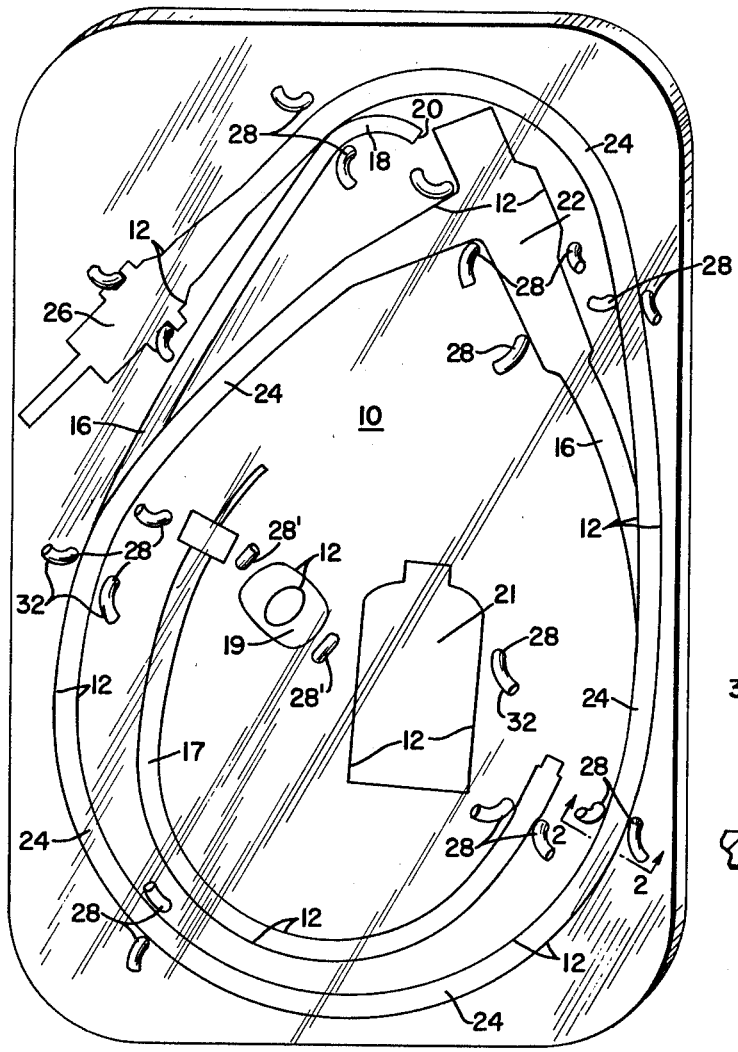
FIG. 1 is a perspective view of a sterilizable holder without the medical instrument to be secured thereon.
Figure 2:
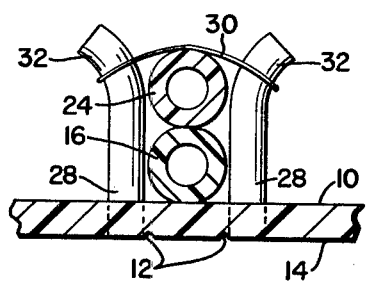
FIG. 2 is a section view taken along lines 2—2 of FIG. 1 illustrating part of a colonofiberscope mounted thereon.

Referring now to the drawings by reference character, a sterilizable holder is illustrated in FIG. 1, having a base 10 of plastics material which is transparent. An outline of the medical instrument to be secured thereon is formed by lines 12, etched or otherwise formed in or printed on the rear surface 14 of the base 10 (FIG. 2). In this instance, the holder is designed to retain a colonofiberscope. Accordingly, a precise outline of the colonofiberscope appears on base 10 so that there is little if any possibility of error when securing the instrument to the holder. Thus the major parts of the colonofiberscope, these being insertion tube 16, bending section 18, distal end 20, control section 22, universal cord 24 and connector 26 appear in the outline. Accessories are outlined at 17, 19 and 21; thus, the colonofiberscope with all attachments and accessories may be mounted on the holder.

A plurality of paired sets of posts or pegs 28 are strategically placed in predetermined fashion about the outline to assure necessary security of all the components of the instrument. After the instrument is placed, a number of elastic or rubber bands 30 (FIG. 2) are secured over each pair of pegs 28. To insure retention of bands 30 on pegs 28 during handling and sterilization of the holder, the distal, free ends of each pair of pegs are bent outwardly as shown at 32.

Pegs 28 may be cemented into mating bores formed in the base, welded thereto or, alternatively, pegs 28 may be threaded with the bores being tapped to receive the pegs.

When the sterilizable holder is used, a surgical wrapping (not shown) is placed on a horizontal surface, whereafter base 10 is placed face or peg side up on the wrapping. The instrument is carefully located thereon between sets of pegs 28 using the outline 12 or 34 as a guide. As illustrated in FIG. 2 wherein a colonofiberscope is to be secured on the holder, the insertion tube 16 will be placed beneath universal cord 24. Then accessories 17, 19 and 21 are placed on their respective outlines. Elastic or rubber bands 30 are placed over each paired set of posts to firmly secure the instrument to base 10. Some posts 28', namely those securing accessories 17, 19 and 21 in place as illustrated in FIG. 1, will be paired with two other posts 28 and thus receive two elastic hands. After this, the entire instrument and holder may be conventionally wrapped (not shown). The entire package may be handled and gas sterilized at temperatures up to 135° F. After sterilization and aeration, the package may be stored on a shelf in its sterile wrapping until needed or the unit may be placed in its original case (not shown).

The wrapped unit may be taken directly to the operating room for use, when needed. The package is simply unwrapped and the rubber bands are removed and disposed of. After use, the unit may be returned to the holder for handling, cleaning, sterilization and subsequent storage.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A sterlizable holder for a fiber optic surgical unit or the like comprising: a flat, horizontal uniplanar base structure constructed of a transparent plastic material; a visually perceived outline of the unit etched on said base on a side thereof opposite that upon which the unit is placed for accurate location of the unit on said base in a predetermined arrangement; a plurality of generally vertically oriented retainer pegs on said base arranged in predetermined paired fashion about said outline; and elastic retainer means adapted to be stretched and slipped over each set of paired pegs to removably secure the unit on said base, the free distal end of each of said pegs being bent outwardly with respect to said outline to assure secure retention of said elastic retainer means over said each set of retainer pegs, all components of said holder being constructed of materials capable of withstanding a gas sterilization process at temperatures up to 135° F.

2. In combination, a fiber optic surgical unit or the like and a sterilizable holder therefor comprising: a flat, horizontal uniplanar base structure constructed of a transparent plastic material; a visually perceived outline of said unit etched on said base on a side thereof opposite that upon which said unit is placed for accurate location of said unit on said base in a predetermined arrangement; a plurality of generally vertically oriented retainer pegs on said base arranged in predetermined paired fashion about said outline; and elastic retainer means adapted to be stretched and slipped over each set of paired pegs to removably secure said unit on said base, the free distal end of each of said pegs being bent outwardly with respect to said outline to assure secure retention of said elastic retainer means over said each set of retainer pegs, all components of said holder and said fiber optic surgical unit being constructed of materials capable of withstanding a gas sterilization process at temperatures up to 135° F.

* * * * *